United States Patent
Ngo et al.

(10) Patent No.: US 7,216,519 B1
(45) Date of Patent: May 15, 2007

(54) STRAIN MONITORING FOR PART QUALITY ANALYSIS

(75) Inventors: Kiet Ngo, London (CA); Paul Hogendoorn, London (CA); Michael Reeve, London (CA)

(73) Assignee: OES, Inc., London, Ontario (CA)

( * ) Notice: Subject to any disclaimer, the term of this patent is extended or adjusted under 35 U.S.C. 154(b) by 0 days.

(21) Appl. No.: 10/892,001

(22) Filed: Jul. 15, 2004

Related U.S. Application Data

(60) Provisional application No. 60/490,663, filed on Jul. 28, 2003.

(51) Int. Cl.
  *B21D 11/22* (2006.01)
  *B21D 55/00* (2006.01)
  *B21D 41/00* (2006.01)

(52) U.S. Cl. .................. 72/21.4; 72/20.4; 72/318

(58) Field of Classification Search .......... 72/20.1, 72/21.4, 318, 31.04
  See application file for complete search history.

(56) References Cited

U.S. PATENT DOCUMENTS

| | | | | |
|---|---|---|---|---|
| 2,152,556 A | * | 3/1939 | Messinger | 33/702 |
| 3,440,848 A | * | 4/1969 | Kramarow et al. | 72/31.01 |
| 4,048,848 A | * | 9/1977 | Dybel | 73/770 |
| 4,062,055 A | * | 12/1977 | Dybel et al. | 361/160 |
| 4,289,022 A | * | 9/1981 | Dybel et al. | 73/862.542 |
| 4,723,429 A | * | 2/1988 | Weber et al. | 72/21.4 |
| 5,092,026 A | * | 3/1992 | Klemmer et al. | 29/593 |
| 5,101,651 A | * | 4/1992 | Yeomans | 72/21.4 |
| 5,937,505 A | * | 8/1999 | Strong et al. | 29/593 |
| 6,718,820 B2 | * | 4/2004 | Kwon et al. | 73/81 |

FOREIGN PATENT DOCUMENTS

WO    WO 03/052533 A1  *  6/2003

* cited by examiner

*Primary Examiner*—Daniel C. Crane
(74) *Attorney, Agent, or Firm*—Carlson, Gaskey & Olds

(57) ABSTRACT

A device for determining the quality of a part includes a sensor for detecting a strain on a selected portion of a part forming machine. A controller utilizes the detected amount of strain to make a determination regarding the quality of a corresponding part. In one example, the sensor detects a compressive or tensile strain on a machine frame when the sensor is aligned to detect a strain parallel to a direction of a force applied during the part formation process. The controller uses one or more characteristics of the sensor output and determines whether the detected amount of strain is within an acceptable range. In one example, monitoring the strain during the formation of a plurality of acceptable parts provides information for determining the acceptable range. The disclosed arrangements allow for making part quality determinations without requiring a sensor to be "in line" with the load.

18 Claims, 2 Drawing Sheets

STRAIN MONITORING FOR PART QUALITY ANALYSIS

CROSS REFERENCE TO RELATED APPLICATIONS

This application claims priority to U.S. Provisional Application No. 60/490,663, which was filed on Jul. 28, 2003.

BACKGROUND OF THE INVENTION

There are a variety of manufacturing processes that require tight tolerances and part quality control. One example is the wire harness industry where wire stripping and crimping operations must be accurate to achieve appropriate and acceptable end products. Another example is the tubing industry and in particular the tubing industry that is related to fluid systems on automotive vehicles.

Typical automobile fluid systems include many tubes and hoses. Example systems include the brake system, fuel system, cooling system, steering system, air conditioning system, among others. Each of these systems handles a specific fluid and typically must operate in a relatively wide range of pressure and temperature conditions. Each of the systems has certain operating parameters that must be met to achieve adequate system operation over the life of the vehicle.

It is important, regardless of the specific system, that the fluid system junctions are 100% reliable for as long as possible. In most instances, the tubes are formed to have a specifically designed end to establish a connection with another portion of the fluid system. The ends of most of the tubes are specially formed to ensure that there are no leaks in the system, even under extreme pressure conditions. In some examples, a hose may be crimped over a formed tube end or the tube may be fastened using a nut compressing a flared end to a mating fitting. In almost all instances, the connection between the tube and the other portion of the fluid system requires the tube end to be specifically and properly formed for that specific purpose. The integrity of the overall fluid handling system depends upon many such tube ends.

Conventional manufacturing processes include forming tube ends using pressing operations on machinery. Appropriate tooling is selected to apply an appropriate amount of force to the raw material to establish the desired end configuration for the tube. A variety of presses and tooling for accomplishing such manufacturing are common.

One method of ensuring appropriate part quality is to inspect the tube ends after the parts are made. This approach has limitations in that it is time consuming, labor intensive and introduces an additional step during the manufacturing process, which reduces the economies of the overall process.

It has not been possible to achieve appropriate measurements during the forming process to obtain part quality information simultaneous with the formation of the parts. One barrier to such an approach has been that it is difficult to obtain a reliable force measurement signal utilizing known force measurement technology. In the wire harness field, for example, a sensor is situated "in line" with the load and is exposed to full load forces. Tube forming processes, however, include peak forces, vibration, speed and other physical factors that make it impractical or not cost-effective for using traditional load sensors for such an application. Additionally, the machine design, variety of machines and the lubricants involved with such machines render traditional sensing arrangements unuseful for the tube end forming process.

Another factor that has contributed to the inability to adequately measure part quality during a tube end forming process is that many tubes have a coating or jacket on an outer surface of the tube. Such coatings or jackets assist in the eventual fluid system reliability, however, they interfere with the ability to accurately measure and compare forces used during end forming operations. Depending on the thickness and integrity of the coating, for example, the forces applied during an end forming operation may appear different because of the coating, which has no necessary connection with the quality of the formed end. Direct peak force measurement is not useful where a tube has a jacket of coating material because a defect in one area may be compensated for by another defect in an unrelated area. For example, a tube with a reduced wall thickness should appear to fail a test, but may pass an inspection test if the coating material was not appropriately stripped in that area such that the coating caused the measured peak force to be inaccurate compared to what it would have been if just the thin-walled metal were present.

There is a need for an improved arrangement that allows for monitoring part quality during a tube end forming process. This invention addresses that need while avoiding the shortcomings and drawbacks of previous attempts.

SUMMARY OF THE INVENTION

An example, disclosed device for determining the quality of a part includes a sensor for detecting a strain on a selected portion of a part forming machine during a part formation process. A controller communicates with the sensor and provides an indication of the quality of the part based on a strain detected by the sensor.

In one example, the sensor responds to a tensile or a compressive strain when the sensor is aligned with a direction of a force applied by a part forming machine. In one example, the sensor provides a strain curve output and the controller uses at least one characteristic of the strain curve output to determine whether the detected strain is within an acceptable range that corresponds to an acceptable part.

An example part forming machine that is disclosed includes a machine frame. A force applying device is useful for applying a force to form a part. The force applying device is supported by the machine frame. A sensor detects a strain on the machine frame during operation of the force applying device. In one example, the sensor includes at least two contact pads that contact the machine frame such that a line between the contact pads is parallel to a direction of the force applied by the force applying device.

An example method of monitoring the quality of a part formation includes determining an amount of strain on a selected portion of a forming machine during the part formation.

The various features and advantages of this invention will become apparent to those skilled in the art from the following description of a currently preferred embodiment. The drawings that accompany the detailed description can be briefly described as follows.

DETAILED DESCRIPTION OF THE PREFERRED EMBODIMENT

Figure 1:
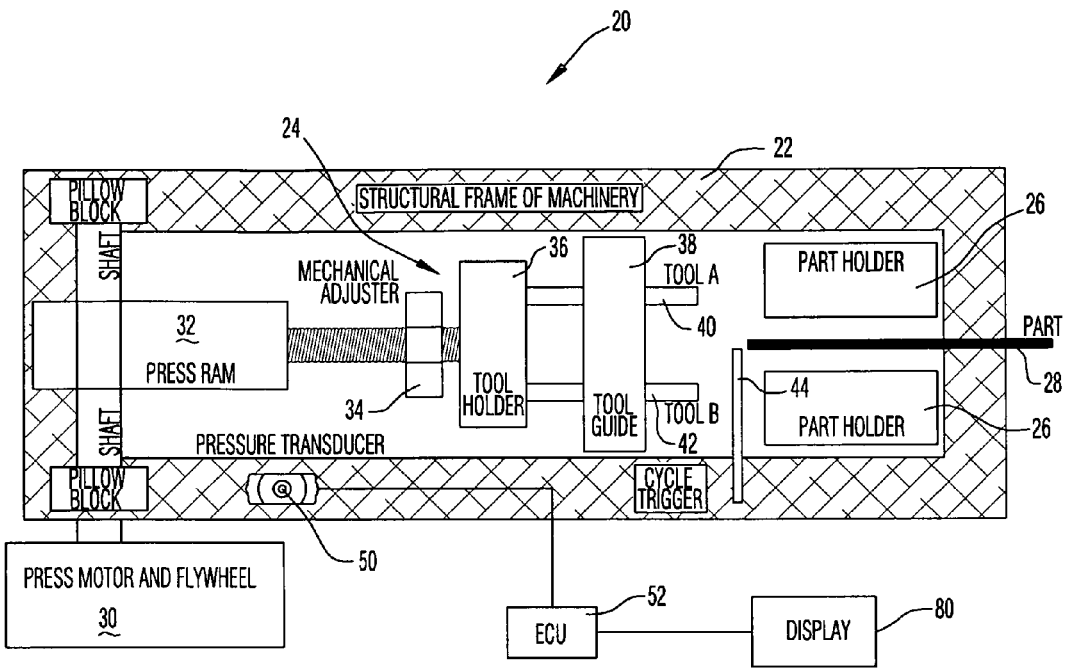
FIG. 1 schematically illustrates a part forming machine including a sensor that detects a stain on the machine during operation of the machine.

FIG. 1 schematically shows a part forming machine 20. A machine body or frame 22 supports various components of the machine including a force applying device 24 and part holding devices 26. A part (i.e., tube stock) 28 is supported by the part holders 26 so that the force applying device 24 can perform the necessary operation to achieve the desired result. Tube end formation is one example part formation that will be discussed below. This invention is not limited to a specific part or part formation.

In the illustrated example, the forming machinery includes a press motor and flywheel 30 that cooperates with a press ram 32 to impart a mechanical force applied to part 28 to form the end as desired. A mechanical adjuster 34, tool holder 36 and tool guide 38 facilitate transferring the force through one or more tools 40, 42 to the part 28. The end-forming components of the machine 20 are generally known. In the illustrated example inserting the part 28 into the machine contacts a cycle switch 44, which releases a clutch that allows the press motor 30 to operate as desired to carry out a tube end forming sequence as known in the art.

The example arrangement includes at least one sensor 50 that provides information to an electronic control unit 52 regarding strain experienced by the machine body or frame 22 during the tube end forming process. In one example, the sensor 50 comprises a micro-strain sensor that is mounted in a selected location on the machine body 22 to provide an indication of the strain level on the machine body, which is an indication of the forces used to form the end of the tube 28. By measuring the micro-strain level of forces transferred into the machine frame 22, the example arrangement allows for measuring the forces associated with forming a tube end in a manner that provides an indication of the quality of the formed tube ends.

Figure 2A:
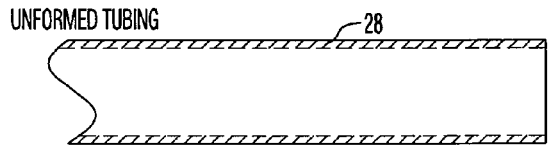
FIGS. 2A–2C schematically illustrate a sequence of steps during a part formation process.
Figure 2B:
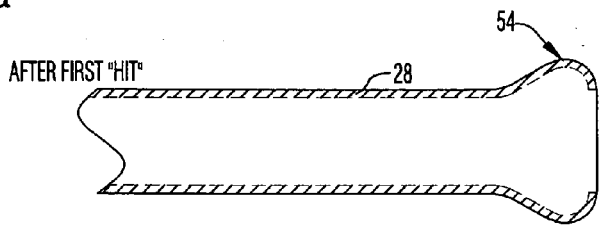
Figure 2C:
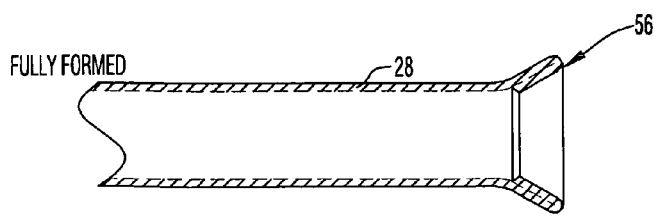

FIG. 2A shows an example part 28 at the beginning of a forming process. FIG. 2B illustrates an example configuration of the tube end 54 after a first tool 40 contacts the tube end responsive to movement of the motor 30. FIG. 2C shows a completed, formed end 56, which results from operation of the tool 42 on the tube end 54 as illustrated in FIG. 2B. The process schematically shown in FIGS. 2A–2C typically involves more than one application of force during the tube end forming process. The example arrangement is capable of measuring the strain on the machinery associated with each of those forces for monitoring the entire tube end forming process and detecting any aberrations from acceptable forces that would indicate whether a part is acceptable. Measuring the micro-strains experienced by the machine frame 22 at each step in the forming process allows the controller 52 to make a part quality determination even though the forces "in line" with the part are not necessarily measured.

Figure 3:
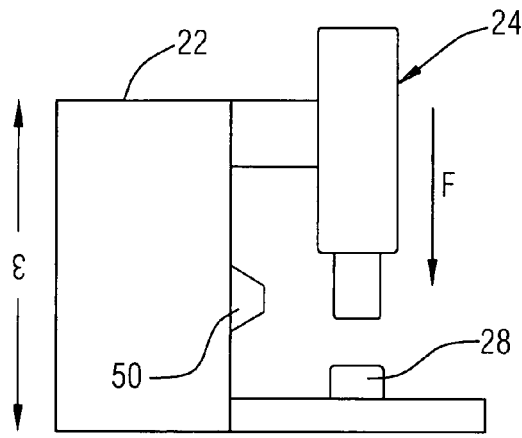
FIG. 3 schematically illustrates another machine arrangement including a sensor that detects a strain on the machine during a part formation process.

In one example, the sensor 50 comprises a piezoelectric micro-strain gauge. When the sensor is positioned on the machine frame 22 such that it detects a strain on the machine frame in a direction parallel to the force applied by the force applying device 24, the sensor 50 detects one of a tensile strain or a compressive strain. Considering the example of FIG. 3, the force arrow F shows the direction of force applied to form the part 28. In that example, the sensor 50 detects a tensile strain on the machine frame 22. If the force arrow were reversed, the sensor 50 would detect a compressive strain.

Figure 4:
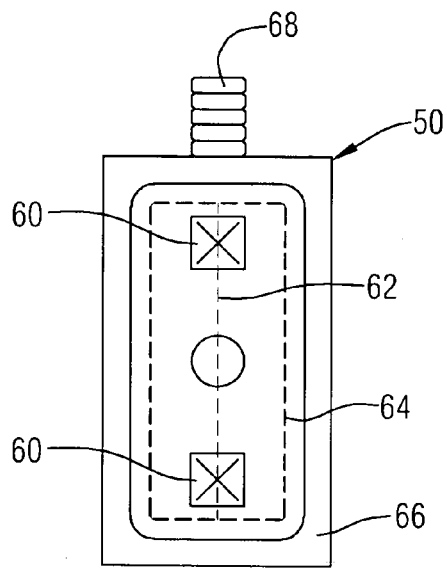
FIG. 4 schematically illustrates selected portions of a sensor useful in the embodiments of FIG. 1 or 3.

FIG. 4 shows one example sensor embodiment where one surface of the sensor 50 includes contact pads 60 that are adapted to be secured against the machine frame 22. When the alignment of the pads 60 is parallel to the direction of the force used during the part formation process, the sensor 50 detects the tensile or compressive strain on the machine frame. In the example of FIG. 4, a centerline 62 of the sensor device 50 corresponds to a line between the centers of the contact pads 60. When the sensor line 62 is aligned in parallel with the direction of the force used to make the part 28, the sensor 50 is able to detect the tensile or compressive strains in a manner that provides correlation between the detected strain and the forces applied to make the part 28. This correlation allows for the example arrangement to provide a reliable part quality indication.

In some examples, a directly parallel alignment is not required, although it is believed to typically provide the most reliable force measurement and the best part quality indication. One example sensor does not include two contact pads and does not necessarily lend itself to a parallel alignment. Various commercially available sensors may be used.

The manner in which the sensor 50 is secured to a machine frame will vary depending on the needs of a particular situation. Those skilled in the art who have the benefit of this description will be able to arrange components in a manner sufficient to provide for adequate contact between the sensor and the machine frame such as by having contact pads 60 flush against an appropriate surface on the machine frame in a selected alignment.

In the example of FIG. 4, the sensor 50 includes a quartz body 64 (shown in phantom). Quartz is one example piezoelectric material that is useful for making a micro-strain gauge, which can be used as a sensor 50 in one of the example arrangements. In this example, the crystal lattice of the quartz body becomes strained because of the tensile or compressive strain detected through the contact pads 60. Charge in the quartz material accumulates at the edge faces of the crystal lattice responsive to the strain. Typically, one end will have an accumulation of positive charge while an opposite end will have a negative charge accumulation. The potential difference between the ends of the crystal lattice, which corresponds to a voltage output from the sensor 50, provides an indication of the amount of strain.

In this example, the sensor 50 is capable of detecting very small amounts of micro-strain. A piezoelectric material such as quartz can be arranged such that appropriate sensitivity for detecting minor fluctuations in strain or force is available. The example of FIG. 4 includes an amplifier and filtering circuitry (not shown) and a connector 68 to provide output signal voltages that are useful to the controller 52 for making a part quality determination.

In one example, the sensitivity of the sensor 50 is measured in terms of millivolts/micro-strain (mV/µε). Larger sensitivity values correspond to more sensitive sensors. One example sensor measures up to 100 µε with a voltage output scale of 100 mV/µε. A typical strain level during one example part formation is between about 30 µε and 100 µε. In one example, the sensor 50 utilizes a supply current of at least several milliamps and is supplied with a voltage of approximately 25 volts DC.

The example sensor is well suited for detecting changes in strain or force. Constant forces may not be discernible in some circumstances. For many part forming operations, applied forces change with time and the position of the tooling in a rapid fashion such that a micro-strain gauge sensor is well-suited to monitor the strain on the machine frame resulting from the forces during a part forming operation.

The electronic control unit 52 preferably is programmed to receive signals from the force sensor 50 and to make determinations regarding the quality of the parts 28 formed during a forming operation.

In one example system, the electronic control unit 52 gathers information during a teach mode regarding the strain imposed on the machinery body or frame 22 during the formation of multiple acceptable parts. The acceptability of the parts may be determined in a separate inspection process, for example. Given the micro-strain data during the formation of acceptable parts, the electronic control unit 52 determines an acceptable range of strain or forces occurring during a forming operation within which it is reasonable to believe that the formed tube end is within acceptable parameters.

Figure 5:
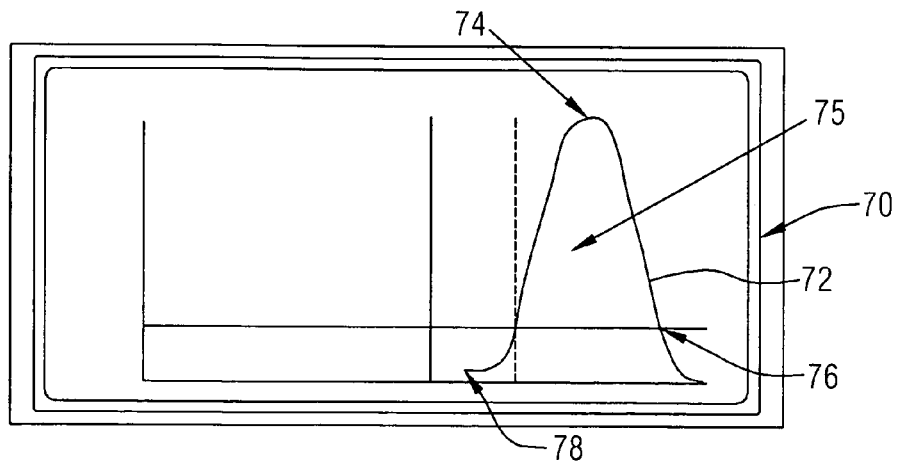
FIG. 5 graphically illustrates an example sensor output.

In one example, the electronic control unit 52 is programmed to monitor a force curve as indicated by the output from the sensor 50. One example output 70 is shown in FIG. 5, which includes a strain curve 72. In one example, the curve indicates strain over time. In another example, the curve shows strain v. tooling displacement.

The example electronic control unit 52 utilizes information regarding the peak of the curve, the area under at least portions of the curve, the standard deviation, another chosen factor, or a combination of more than one of these as a control parameter for determining whether a detected strain during a part forming process fits within an acceptable tolerance range.

In this example, the controller 50 utilizes a plurality of characteristics of the strain curve 72 for making a determination regarding the quality of a corresponding part. In one example where the force applying device tooling does not bottom out, a peak 74 of the curve 72 provides information regarding the maximum amount of force applied by the part forming device 24. An area 75 beneath the curve 72 above a reference value 76 provides information regarding the way in which the force was applied as the force applying device 24 is in working contact with the part 28. The reference value 76 corresponds to a point in time or space where the force applying device is beginning the formation (i.e., beginning to alter the shape of) the part 28. In this example, the controller 52 also determines an area factor associated with a portion of the curve 72 shown at 78, which is below the reference value 76 in this example. In this example, the area factor at 78 provides information about the way in which the force is applied to the part 28 when the force applying device 24 initially makes contact with the part 28.

In one example, each of the above-described factors, which can be determined from the strain curve 72, provides information regarding the quality of a part. If the obtained values (or a relationship between them) are within an acceptable range, the part is judged as acceptable.

In another example, the tooling bottoms out during the part formation process and the controller 52 does not utilize the peak value at 74 as part of the analysis. In such an example, only the portions of the curve prior to the peak 74 are of interest.

Those skilled in the art who have the benefit of this description will be able to select a curve analysis that meets their particular needs.

One example arrangement includes an interface 80 (FIG. 1) to provide an indication of the acceptability of the part, given the detected amount of strain. In one example, the interface 80 comprises a display screen. In another example, the interface 80 comprises a printing device that provides a hard copy of an indication regarding the acceptability of a part. Those skilled in the art who have the benefit of this description will be able to determine appropriate ranges to meet the tolerance requirements of their particular situation.

In situations such as that schematically shown in FIGS. 2A–2C, multiple force applications are required for forming the eventual part 28. In such an example, the sensor 50 provides multiple strain curve outputs, each strain curve corresponding to each application of force. The controller 52 utilizes each of the curves to make the overall part formation determination in one example. The number of force applications to be monitored for forming a particular part will depend upon the needs of a particular situation. The example arrangement is capable of providing information regarding one or any number of force applications during a part formation process such that the detected strain on the machine provides an indication of the quality of the part.

The example arrangement has the capacity for detecting simple or complex failure conditions such as broken tooling, misaligned tooling, defective raw material, improperly located raw material and interrupted processes. Other possible failure conditions that are discernible include worn tooling, improperly stripped coating or jacket conditions, machinery maintenance issues (i.e., bearing conditions, motor conditions, mechanical looseness, belts, etc.) and improperly presented material. The disclosed example also makes it possible to detect process deviations that may eventually lead to production errors before such errors occur. The inventive arrangement provides an enhanced ability to discern even minor defects during a manufacturing process that would not be discernible in a post-manufacturing inspection.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A part forming machine, comprising:
   a machine frame;
   a force applying device for applying a force to form a part, the force applying device being supported by the machine frame; and
   a sensor that detects a strain on the machine frame during operation of the force applying device
   a controller that communicates with the sensor and determines whether the detected strain is within an acceptable range; and
   wherein the sensor provides a strain curve output indicative of at least one force application during a forming of a single part and the controller uses at least an area under a selected portion of the strain curve output to determine whether a corresponding portion of the detected strain is within the acceptable range.

2. The machine of claim 1, wherein the sensor is supported on the frame such that the sensor detects the strain in a direction that is parallel to a direction of the force applied by the force applying device.

3. The machine of claim 2, wherein the sensor includes at least two contact pads that contact the machine frame such that a line between the contact pads is parallel to the direction of the force.

4. The machine of claim 1, wherein the controller uses a peak of the strain curve output to determine a maximum strain.

5. The machine of claim 1, including an interface that provides an indication of whether a part is acceptable based upon the detected strain.

6. The machine of claim 1, wherein the controller uses the area under the selected portion of the strain curve output that occurs prior to the curve reaching a reference value to determine information about a way that a force was applied during an initial contact between the force applying device and the single part.

7. The machine of claim 1, wherein the controller uses an area of a selected portion of the strain curve output above a reference value to determine information about a way that a force was applied as the force applying device was in working contact with the single part.

8. The machine of claim 7, wherein the reference value corresponds to a point in time or space where the force applying device begins the formation of the single part.

9. A device for determining a quality of a part, comprising:
   a sensor for detecting a strain on a selected portion of a part forming machine during a part formation process;
   a controller that communicates with the sensor and provides an indication of the quality of the part based on a strain detected by the sensor; and
   wherein the sensor provides a strain curve output corresponding to at least one force application during a single part formation and the controller uses at least an area under a selected portion of the strain curve output to determine whether a corresponding portion of the detected strain is within an acceptable range.

10. The device of claim 9, wherein the controller uses a peak of the strain curve output to determine a maximum strain.

11. The device of claim 9, including an interface that provides an indication of whether a part is acceptable based upon the detected strain.

12. The device of claim 9, wherein the controller uses the area under the selected portion of the strain curve output that occurs prior to the curve reaching a reference value to determine information about a way that a force was applied during an initial contact with the single part.

13. The device of claim 9, wherein the controller uses an area of a selected portion of the strain curve output above a reference value to determine information about a way that a force was applied during working contact with the single part.

14. The device of claim 13, wherein the reference value corresponds to a point in time or space associated with a beginning of an alteration of a shape of the single part.

15. A method of monitoring the quality of a part formation, comprising:
   determining an amount of strain on a frame of a forming machine during a single part formation from an area under a selected portion of a curve that is indicative of the strain associated with changes in a force applied during a corresponding portion of the single part formation;
   using a sensor for detecting the strain associated with changes in the force applied during the single part formation; and
   automatically generating the curve from an output of the sensor.

16. The method of claim 15, wherein the area under the selected portion of the curve occurs prior to the curve reaching a reference value and comprising
   determining information about a way that a force was applied during an initial contact with the single part.

17. The method of claim 15, wherein the area under the selected portion of the curve is above a reference value and comprising
   determining information about a way that a force was applied as the forming machine was in working contact with the single part.

18. The method of claim 17, wherein the reference value corresponds to a point in time or space associated with a beginning of an alteration of a shape of the single part.

* * * * *